United States Patent [19]

Mattes et al.

[11] Patent Number: 5,143,843
[45] Date of Patent: Sep. 1, 1992

[54] METHOD FOR PRODUCTION OF MONOCLONAL ANTIBODIES FOR CANCER DIAGNOSIS AND THERAPY

[75] Inventors: M. Jules Mattes, Flushing; Lloyd J. Old, New York; Kenneth O. Lloyd, Bronx, all of N.Y.

[73] Assignee: Sloan-Kettering Institute For Cancer Research, New York, N.Y.

[21] Appl. No.: 732,724

[22] Filed: Jul. 18, 1991

Related U.S. Application Data

[63] Continuation of Ser. No. 556,860, Jul. 19, 1990, abandoned, which is a continuation of Ser. No. 12,267, Feb. 9, 1987, abandoned, which is a continuation of Ser. No. 556,579, Nov. 30, 1983, abandoned.

[51] Int. Cl.$^5$ .................. C12N 5/20; C07K 15/28
[52] U.S. Cl. .................. 530/388.85; 424/85.8; 424/85.91; 435/70.21; 435/172.2; 435/240.27; 935/104; 935/107; 935/108; 935/110
[58] Field of Search .................. 530/387-388; 424/85.8, 88; 435/70.21, 172.2, 240.27; 935/104, 107, 108

[56] References Cited

U.S. PATENT DOCUMENTS

| | | | |
|---|---|---|---|
| 4,471,057 | 9/1984 | Koprowski et al. | 436/518 |
| 4,517,289 | 5/1985 | Milford et al. | 435/7.23 |
| 4,522,918 | 6/1985 | Schlom et al. | 435/68.1 |
| 4,591,572 | 5/1986 | Mattes et al. | 530/387 |
| 4,650,756 | 3/1987 | Old et al. | 435/68 |

OTHER PUBLICATIONS

Cairncross et al., "Cell Surface Antigens of Human Astrocytoma Defined by Mouse Monoclonal Antibodies: Identification of Astrocytoma Subsets", *Proc. Natl. Acad. Sci. USA*, 79:5641–5645, Sep. 1982.

Steplewski, Z., "Monoclonal Antibodies to Human Tumor Antigens", *Human Tumor Antigens*, Grune & Stratton, Inc., pp. 384–387, 1980.

Mattes et al., "Monoclonal Antibodies to Three Widely Distributed Human Cell Surface Antigens", *Hybridoma* 3(2):253–264, Dec. 1983.

Dippold et al., *PNAS* 77(10) 1980, pp. 6114–6118.
Burchiel et al., *Cancer Res.* 42, 1982, pp. 4110–4115.
Seeger et al., *Cancer Res.* 41, 1981, pp. 2714–2717.
Colcher et al., *PNAS* 78(5) 1981, pp. 3199–3203.

*Primary Examiner*—John Doll
*Assistant Examiner*—Robert D. Budens
*Attorney, Agent, or Firm*—John P. White

[57] ABSTRACT

Monoclonal antibodies to human antigens present on a majority of human cells are described. These mAbs have use in a method for isolating mAb for less expressive antigens, such as cancer antigens, or other antigens associated with particular abnormalities, disorders or disease state. The latter mAbs may be weaker than or not present to such an extent as the first mentioned mAbs. For example, these less expressive mAbs would be useful for cancer diagnosis, especially in the early stages, and for cancer treatment as well where the cancer cell is the target cell for the mAb. The mAb can be tagged with a tissue destructive agent such as a radiolabel, a toxin, a chemical poisen, and the like. Some of the mAbs described, subset tumors of particular types and so are useful for tumor subclassification. The mAbs described are also useful in analyzing the properties and functions of their respective antigens in human cells.

6 Claims, No Drawings

METHOD FOR PRODUCTION OF MONOCLONAL ANTIBODIES FOR CANCER DIAGNOSIS AND THERAPY

This invention was partially made with funds provided by the National Cancer Institute under grants CS-26184, CA19765 and CA-08748. Accordingly, the U.S. Government has certain rights in this invention.

This is a continuation of application Ser. No. 556,860, filed Jul. 19,1990, now abandoned which is a continuation of Ser. No. 07/012,267 filed Feb. 9, 1987, which is a continuation of Ser. No. 07/556,579 filed Nov. 30, 1983, now abandoned.

This invention relates to a method for the production of monoclonal antibodies (mAbs) to more weakly antigenic human cell components by preparing mAb to strongly immunogenic human antigen(s) which mAb clears out the strong antigen component(s) of subsequent immunogens. Thus expression of these more weakly expressed antigenic components is enhanced. Such mAbs have use in cancer diagnosis and therapy, as well as other cell disorders.

BACKGROUND

Conventional antisera, produced by immunizing animals with tumor cells or other antigens, contain a myriad of different antibodies differing in their specificity and properties. In 1975 Köhler and Milstein (Nature, 256:495) introduced a procedure which leads to the production of quantities of antibodies of precise and reproducible specificity. The Köhler-Milstein procedure involves the fusion of spleen cells (from an immunized animal) with an immortal myeloma cell line. By antibody testing of the fused cells (hybridomas), clones of the hybridomas are selected that produce antibody of the desired specificity. Each clone continues to produce only that one antibody, monoclonal antibody (mAb). As hybrodoma cells can be cultured indefinitely (or stored frozen in liquid nitrogen), a constant, adequate supply of antibody with uniform characteristics is assured.

Antibodies are proteins that have the ability to combined with and recognize other molecules, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available.

The preparation of hybridoma cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Process in defining cell surface antigens is of great importance in differentiation and disease as markers for normal and diseased cells, thereby furthering diagnosis and treatment. Thus work on melanocytes was made possible by the recently discovered technique of culturing melanocytes from normal skin (Eisinger, et al., Proc. Nat'l. Acad. Sci. U.S.A., 79 2018 (Mar. 1982). This method provides a renewable source of proliferating cells for the analysis of melanocyte differentiation antigens. Likewise, a large number of cell lines derived from melanomas have now been established and these have facilitated the analysis of melanoma surface antigens. The advent of mAbs has greatly accelerated knowledge about the surface antigens of malignant melanoma. cell markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. [Dippold et al. *Proc. Nat'l. Acad. Sci. U.S.A.* 77, 6114 (1980) and Houghton, et al. *J. Exp. Med.* 156, 1755, (1982)]. Immunoassy of melanocytes and melanoma cells within sub-sets is thus made possible.

Initial recognition of differentiation antigens came about through analysis of surface antigens of T-cell leukemias of the mouse and the description of the TL, Thy-1, and Lyt series of antigens. (Old, Lloyd J., Cancer Research, 41, 361-375, Feb. 1981) The analysis of these T-cell differentiation antigens was greatly simplified by the availability of normal T cells and B cells of mouse and man. (See Patents #4,361,549-559; #4,3643,932-37 and #4,363,799 concerning mAb to Human T-cell antigens).

The existence of human leukemia specific antigens has been suggested by studies using heterologous antibodies developed by immunization with human leukemic cells [Greaves, M. F. et al. Clin. Immunol. and Immunopathol 4:67, (1975); Minowada, J., et al. J. Nat'l. Cancer Insti. 60:1269, (1978); Tanigaki, N., et al. J. Immunol. 123:2906, (1979)] or by using autologous antisera obtained from patients with leukemia [Garret, T. J., et al., Proc. Nat'l. Acad. Sci. U.S.A. 74:4587, (1977); Naito, K., et al., Proc. Nat'l. Acad. Sci. U.S.A., 80: 2341, (1983)]. The common acute lymphoblastic leukemia antigen (CALLA) which is present on leukemia cells from many patients with non-T, non-B, acute lymphoblastic leukemia (N-ALL), some chronic myelocytic leukemias (CML) in blast crisis and a few acute T-lymphoblastic leukemias (T-ALL) was originally described using conventional rabbit heteroantisera [Greaves, M. F. et al. Supra]. By the autologous typing technique [Garret, T. J., et al. Supra; Naito, K., et al. Supra 1983; Old, L. J. Cancer Res. 41:361, (1981)], antibodies uniquely reacting with ALL cells were found in sera obtained from patients with ALL, and seemed to recognize very similar antigens to CALLA (Garret, T. J., et al. Supra; Naito, K., et al. Supra). Another leukemia associated antigen detected by heterologous antisera is the human thymus leukemia (TL)-like antigen, which is present on thymocytes as well as leukemia cells (Tanigaki, N. et al. Supra). This antigen, is therefore, a normal differentiation antigen which is composed of a heavy chain (MW 44,000–49,000 ) and light chain (MW 12,000–14,000) similar to the class I HLA antigens (Tanigaki, N., et al. Supra). These investigations have, however, been hampered by the need for vigorous absorptions with normal tissues as well as the relatively small quantity and low titer of the antisera.

In vitro production of monoclonal antibodies by the technique of Köhler and Milstein, Supra has provided a better system for the identification and detection of leukemia specific antigens. A panel of monoclonal antibodies detecting cell surface antigens of human peripheral blood lymphocytes and their precursor cells have been investigated in detail [Reinherz, E. L., et al. Proc. Nat'l. Acad. Sci. U.S.A. 77:1588, (1980)]. While monoclonal antibodies detecting antigens characteristic for different lymphocyte lineages can be used for classification of human lymphocytic leukemia [Schroff, R. W., et al. Blood 59: 207, (1982)], such antibodies have only limited therapeutic applications. Monoclonal antibodies detecting human leukemia associated antigens have also been produced. These include several antibodies detecting the human equivalents of the murine TL antigens. One TL-like antigen is recognized by Na1/34 [McMichael, A. J., et al. Eur. J. Immunol. 9:205, (1979)], OKT6 (Reinherz, E. L., et al. Supra) and Leu 6 (R. Evans, personal communication). A second TL-like antigen is recognized by M241 (Knowles, R. W., et al. Eur. J. Immunol. 12: 676,1982). Monoclonal antibodies with specificities for common acute lymphoblastic leukemia antigens J-5 (Ritz, J., et al. Nature 283:583, 1980), NL-1 and NL-22 (Ueda, R., et al. Proc. Nat'l. Acad. Sci. U.S.A. 79:4386, 1982) have also been produced. Recently, Deng, C-T, et al. Lancet. i:10, 1982) reported a complement fixing monoclonal antibody (CALLA-2) which reacts with most cultured human T-ALL cell lines and also reacts with most fresh T-ALL cells.

Mouse monoclonal antibodies to human tumor cell surface antigens have been produced in many laboratories (Lloyd, K. O. (1983) In: Basic and Clinical tumor Immunology, Vol. 1 (R. B. Herberman, Ec.), Nijhoff, The Hague (in press)). The intention of these studies often has been to identify tumor-associated antigens that could be useful in tumor therapy or diagnosis. An inherent difficulty in this approach is the diversity of antigens on the cell surface. Although it has been possible to identify some antigens with a very restricted distribution, antibodies to antigens that elicity very weak immune responses may be missed due to their scarcity. Also, immunization with a complex mixture of antigens such as tumor cells may suppress the antibody response to relatively less immunogenic molecules, in a manner resembling antigenic competition (Taussig, M. J. (1973). Curr. Top. Micro. Immuno. 60:125). One approach to circumvent these difficulties is to prepare antibodies to the strongly immunogenic antigens and to use them to remove those antigens from subsequent immunogens; this approach has been designated the "cascade" procedure (Springer, T. A. (1981) J. Biol. Chem. 256:3833) since it allows the generation of new antibodies, different from those previously obtained. The present invention provides for cancer diagnosis and therapy and overcomes problems heretofor encountered in the prior art.

SUMMARY

In this invention, mouse monoclonal antibodies to very common glycoprotein antigens that are present on most or all human cells are produced. These antibodies are useful in producing cancer specific mAbs for diagnosis and therapy, and, in analyzing the properties and functions of their respective antigens in human cells. Furthermore, these widely distributed monoclonal antibodies can be used to produce other monoclonal antibodies which recognize more weakly antigenic cell antigens specific to other cell disorders thereby enabling diagnosis and/or treatment of said disorders with the monoclonal antibody to the specific cell antigen. These disorder-specific, or cancer-specific, or weakly antigenic-specific mAbs find enhanced expression after immunization with immunogen from which strong antigens have been removed by mAb to strong antigenic determinants.

DESCRIPTION

The techniques described below resulted in isolation of specific mAbs recognizing antigen present on a majority if not all human cell lines tested. The specific monoclonal antibodies described in the examples below are each representative of a class of mAb with similar characteristics produced and isolated by the method of the invention. This illustrates the general utility of the method. The method of the invention can readily be used to isolate other such mAbs in order to obtain the mAb expression of more weakly antigenic components and/or those antigenic components present in low concentration in or in cells. These more like antigenic components may have their antigenicity masked by those antigens present on a majority if not all cell lines. Raising mAb to weak antigens specific for cell types and/or cell disorders or abnormalities can lead to use of these mAb weak antigens for diagnostic purposes. They will only react with their specific antigenic site and are thus useful for diagnosis. As for therapy such mAb to the weaker antigenic sites can be conjugated to radioactive moieties or cellular poisen(s) in order to kill disorder-specific or abnormal cells, as for example, cancer cells.

The mAbs to widely distributed and/or strong antigens can be used to deactivate or remove the antigen as for example, the widely distributed mAbs can be conjugated to sepharose beads or *staphylococcus aureus* to remove or deactivate the respective widely distributed antigen from detergent-solubilized cell extracts. Thus removal of the widely distributed and/or strong antigen can be effected by standard method sin immunology using affinity columns. See Spring, Supra The remaining deactivated immunogen material not so removed can be used to immunize other mammals in order to produce new mAbs since the strong antigenic site has been deactivated. Such steps may be repeated as many times as needed to produce still more new mAbs from successively or progressively weaker antigenic components of successive immunogens. Such antigen removal may be effected with several different immunogens each of which contains the same widely distributed antigen(s). Mixtures of mAbs to strong antigens may be used as well. Thus, the mAb examples of the invention are for illustration purposes and are not meant to limit the invention to the mAb examples described. The description of the specific example is found in the Nov. 1983 edition of Hybridoma (in press) in an article entitled "Monoclona Antibodies to Three Widely Distributed Human Cell Surface Antigens", which article is incorporated by reference.

Target cells

Cell lines used are listed in Table I below. Preparation of cultures of normal human fibroblasts, kidney epithelial cells and melanocytes have been described (Carey, T. E., et al. Proc. Nat'l. Acad. Sci. U.S.A. 73:3278; Ueda, R., et al. (1979) J. Exp. Med. 150:564; Eisinger, M., et al. (1982) Proc. Nat'l. Acad. Sci. U.S.A. 79:2018). Adherent cells were maintained in Eagle's Minimum Essential Medium (GIBCO, Grand Island, N.Y.) supplemented with 2.5% fetal calf serum, 5% newborn calf serum, 100 units/ml penicillin and 1 mg/ml streptomuycin.

TABLE 1

| Target cell lines | | |
|---|---|---|
| Ovarian carcinomas | Renal carcinomas | Lung carcinomas |
| SK-OV-3[a] | SK-RC-4[a] | SK-LC-1[a] |
| SK-OV-4[a] | SK-RC-6[a] | SK-LC-2[a] |
| SK-OV-6[a] | SK-RC-7[a] | SK-LC-3[a] |
| Colo 316[a] | SK-RC-9[a] | SK-LC-4[a] |
| 2774[a] | SK-RC-12[a] | SK-LC-5[a] |
| A7[a] | SK-RC-16[a] | SK-LC-6[a] |
| A10[a] | SK-RC-28[a] | SK-LC-7[a] |
| SW626[a] | SK-RC-29[a] | SK-LC-8[a] |
| Breast carcinomas | SK-RC-35[a] | SK-LC-9[a] |
| SK-BR-3[a] | SK-RC-1 | SK-LC-10[a] |
| SK-BR-5[a] | SK-RC-2 | SK-LC-13[a] |
| BT-20[a] | SK-RC-8 | SK-LC-14[a] |
| BT-474[a] | SK-RC-10 | SK-LC-15[a] |
| MCF-7[a] | SK-RC-17 | SK-LC-16[a] |
| AlAb[a] | Caki-1 | Calu-1[a] |
| ZR-75-1[a] | Caki-2 | SK-LC-LL[a] |
| CAMA[a] | Teratocarcinomas | SK-LC-12 |
| MDA-MB-361 | Tera-2[a] | Astrocytomas |
| MDA-MB-231 | 557M-F[a] | SK-MG-1 |
| Bladder carcinomas | 833K[a] | SK-MG-1 |
| Scaber[a] | Pancreatic carcinomas | SK-MG-2 |
| RT4[a] | CAPAN-1[a] | SK-MG-3 |
| VM-CUB-1[a] | CAPAN-2[a] | SK-MG-5 |
| VM-CUB-2[a] | ASPC-1[a] | SK-MG-6 |
| 5637[a] | Melanomas | SK-MG-8 |
| 639-V[a] | SK-MEL-13 | SK-MG-9 |
| 253J | SK-MEL-19 | SK-MG-10 |
| J82 | SK-MEL-23 | SK-MG-11 |
| 486-P | SK-MEL-26 | SK-MG-14 |
| TCC-SUP | SK-MEL-28 | SK-MG-15 |
| Colon carcinomas | SK-MEL-29 | AE |
| SK-CO-1[a] | SK-MEL-31 | CJ |
| SW403[a] | SK-MEL-37 | U138MG |
| SW480[a] | SK-MEL-75* | U251MG |
| SW620[a] | SK-MEL-93-2 | U343MG |
| SW1222[a] | SK-MEL-93-3 | U373MG |
| HT29[a] | SK-MEL-127 | A-382 |
| SK-CO-10[a] | SK-MEL-130 | |
| | SK-MEL-153 | |
| | MeWo | |
| Other carsinomas | B cell lymphomas and leukemias | |
| SK-Hep-1 | SK-LY-16 | |
| (hepatome) | SK-Ly-18 | |
| ME180[a] | Daudi | |
| (cervical) | Ball-1 | |
| SK-UT-1[a] | SK-DHL-2 | |
| (uterine) | ARA-10 | |
| GCC-SV(C)[a] | Raji | |
| (choriocar- | T cell lymphomas and leukemias | |
| cinoma) | MOLT-4[a] | |
| Neuroblastomas | CCRF-HSB-2[a] | |
| SK-N-SH[a] | CCRF-CEM[a] | |
| SK-N-MC[a] | 45[a] | |
| LA-N-ls[a] | 8402 | |
| SH-EP₁[a] | Peer | |
| BE (2)-C | P-12/Ichikawa | |
| SK-N-BE(2) | HPB-ALL | |
| Null cell leukemias | Normal cells | |
| NALM-16 | 1 skin fibroblast[a] | |
| NALL-1 | 3 lung fibroblast[a] | |
| Myeloid leukemias | 1 fetal lung | |
| HL-60[a] | fibroblast[a] | |
| K562 | 1 umbilical cord | |
| KG-1 | fibroblast | |
| Myelomas | 2 kidney epithelial[a] | |

TABLE 1-continued

| Target cell lines | |
|---|---|
| SK-MY-1 | 1 melanocyte |
| LICR-Lon-HMy-2 | Non-human cells |
| Monocytoid cell line | VERO (monkey kidney)[a] |
| U937 | CHO (chinese hamster ovary) |

[a]Positive for MH99. Other cell lines were negative.

For passage, cells were detached with 0.1% trypsin, 0.02% ethylene diamine tetra-acetic acid in Hank's salt solution without divalent cations (GIBCO). Non-adherent cells were cultured in RPMI 1640 medium supplemented similarly except with 7.5% fetal calf serum. Cultures were regularly tested for mycoplasma and contaminated cultures discarded.

Normal blood mononuclear cells were obtained by centrifuging heparinized blood onto a layer of Ficoll-Paque (Pharmacia, Piscataway, N.J.). Total blood leukocytes were obtained by collecting the buffy coat after centrifugation for 10 minutes at 600 g in 100 microliter capillary tubes.

Production of mouse monoclonal antibodies

BALB/c or (BALB/c×C57BL/6)F₁ mice were immunized with either the astrocytoma SK-MG-1, the ovarian carcinoma SK-OV-3 or the uterine carcinoma SK-UT-1. Intraperitoneal injections of approximately 100 microliters of packed cells were given 2–5 times at intervals of 2 weeks. Three day after the last injection, the fusion of immune spleen cells with mouse myeloma MOPDC-21 NA/1 cells was performed as described (Dippold, W. G., et al. (1980) Proc. Nat'l. Acad. Sci. U.S.A. 77:6614). Initially cells were plated in 480 wells (Costar No. #3524, 24 well plates). Hybridoma cultures were subcloned at least 2 times by limiting dilution in 96-well plates on a feeder layer of normal mouse spleen cells. Culture supernatants were monitored for antibody activity by the anti-mouse Ig MHA method on a panel of cultured cells consisting of the immunizing cell line and other types of human tumor cells. Cloned hybridoma cells were injected subcutaneously into nu/nu mice. Sera from mice with progressively growing tumors were collected and used for serological and biochemical characterization. Antibody subclass was determined by double diffusion in agar with anti-Ig heavy-chain-specific reagents (Bionetics, Kensington, Md.).

MAb derived from mice serve as illustration of the method. It is obvious to those skilled in the art that the method is not specific to mice but can be used to derive mAb from any species to which hybridoma methods can be adapted.

Serological procedures

For adherent target cells, 200–500 trypsinized cells were plated in 10 microliters in wells of Terasaki plates (Falcon Microtest plates 3034) and allowed to adhere overnight. Non-adherent target cells were attached to the wells by pretreating the wells for 45 minutes at room temperature with 10 microliters Concanavalin A (Con A, grade IV, Sigma Chemicals, St. Louis, Mo.) at 1.0 mg/ml in Dulbecco's Phosphate buffered saline (PBS) (DPBS, GIBCO). After washing the plates-twice and blotting, target cells in DPBS were added and incubated for 45 minutes at room temperature.

The immune rosetting (anti-mouse Ig MHA) has been described (Ueda, R., (1979) Supra). The CrCl₃ conjugation procedure has been described (Koo, G. C., et al. (1978) J. Immunol. Meth. 23:197), except that undiluted rabbit anti-mouse IgG (DAKO, Accurate Chemicals, Westbury, N.Y.) was used instead of Protein A. Monoclonal sera were titrated starting at $10^{-3}$. Absorption procedures have also been described (Carey, T. E., et al. (1976) Supra).

Immunoperoxidase staining of sections employed 5 micrometer cryostat sections. Air-dried sections were fixed for 10 minutes at room temperature with 2.0% buffered formaldehyde (Farr, A. G., et al. (1981) J. Immunol. Meth. 47:129). Sections were obtained from specimens of normal human liver, kidney, lung, pancreas, brain, skin, colon, thyroid, testes, uterus, ovary, spleen and lymph node, and from ovarian carcinomas. A triple sandwich was used routinely, which comprised monoclonal sera at 1/500, biotinylated horse anti-mouse Ig, and complexes of avidin and biotinylated horseradish peroxides (Vectastain reagents, Vector Laboratories, Burlingame, Ca.), following procedures recommended by the manufacturer. For particular tissues that had excessive background with this procedure, namely the kidney, liver, and pancreas, a double sandwich was used which comprised monoclonal sera at 1/200 and peroxides-conjugated rabbit anti-mouse Ig (DAKO P161) at 1/50.

Immunofluorescent staining of blood leukocytes in suspension was performed as described (Mattes, M. J., et al. (1979) J. Immunol. 123:2851) using fluorescein-conjugated goat anti-mouse Ig (Cappel Laboratories, Cochranville, Pa.) at 1/40 and monoclonal sera at 1/50. Lymphocytes and granulocytes were distinguished by morphology.

Immunoprecipitation procedures

Each antibody was tested for its ability to precipitate an antigen from detergent-solubilized extracts of the immunizing cell after labeling by three methods: metabolic incorporation of [$^3$H]glucosamine (Ogata, S-I, et al. (1981) Proc. Nat'l. Acad. Sci. U.S.A. 78:770), metabolic incorporation of [$^{35}$S]methionine (Cairncross, J. G., et al. (1982) Proc. Nat'l. Acad. Sci. U.S.A. 79:5641), or chloramine T $^{125}$I-labeling of solubilized cell membranes (Cairncross, J. G., (1982) Supra). NP40 solubilization of labeled cells and Concanavalin A (Con A)-Sepharose fractionation of labeled extracts, used in some experiments, have been described (Cairncross, J. G., (1982) Supra; Lloyd, K. O., et al. (1981) J. Immunol. 126:2408). Immunoprecipitation procedures for $^{125}$I-labeled samples, using *Staphylococcus aureus*, have been described (Cairncross, J. G., et al. (1982) Supra). Aliquots of $2\times 10^6$ cpm $^{35}$S from unfractionated cell extracts were handled similarly except pre-clearing was omitted. For the Con A eluate fraction of $^{35}$S-labeled extracts and for $^3$H-labeled extracts, aliquots of $2\times 10^5$ cpm and different washing buffers (Lloyd, K. O., et al. (1981) Supra) were used.

Precipitated molecules were extracted with 60 microliters 0.01 M Tris HCl pH 7.2, 2.0% sodium dodecylsulfate (SDS), 12.0 mg/ml dithiothreitol (DTT), 15% (wgt/vol) sucrose, 0.01% pyronin Y by heating 5 minutes at 100° C., and analyzed by polyacrylamide gel electrophoresis (PAGE) (Laemmli, U. K. (1970) Nature 227:6870), using 9% gels. For 2-dimensional electrophoresis (isoelectric focusing followed by SDS-electrophoresis) immune precipitates were extracted and handled as described (Ogata, S-I, et al. (1981) Supra; O'Farrell, P. H., jet al. (1977) In: Methods in Cell Biology (Prescott, D. M., ed.) Academic Press, N. Y., Vol, 16, pp. 407–420). For unreduced samples, DTT was omitted and 14.0 mg/ml idoacetamide was added to samples.

SELECTION OF HYBRIDOMAS—EXAMPLES

Monoclonal antibodies of the class represented by MA103 and MA99 were obtained from fusions of the spleen cells of mice immunized with SK-OV-3 (ovarian carcinoma). MAb of the class represented by MH99 was obtained from immunizations with SK-UT-1 (endometrial carcinoma). The derivation of mAb AJ2 from mice immunized with the astrocytoma cell line SK-MG-1 has been described previously (Cairncross, J. G., (1982) Supra). The heavy chain subclasses were determined to be gamma sub 2a for mAb MA103, gamma sub 1 for mAb MA99, gamma sub 2a for mAb MH99 and gamma sub 1 for mAb AJ2. mAb AJ2 and mAb MA103 were found to react with all target cells tested in the initial screening of a panel of human tumor cells. mAb MH99 was found to react with the immunizing carcinoma and a variety of other cell types but not with melanomas or astrocytomas.

Examples of antigen detected by mAb examples above:

EXAMPLE 1: AJ2

The AJ2 antigen detected by mAb AJ2 was present on all 140 cell lines tested by immune rosetting including both normal and malignant cells (Table I). VERO monkey cells were also positive, while CHO hamster cells were negative. the titer in rosetting assays was usually $10^{-5}-10^{-6}$. The AJ2 antigen could not be detected on erythrocytes by absorption analysis. By immunofluorescence, the antigen was detected on at least 70–80% of normal human blood mononuclear cells, but since the staining was relatively weak, it is uncertain whether there is a distinct negative cell population. The antigen was also detected in sections man. (See Patents No. 4,361,549-559; No. 4, of all 13 normal human tissues examined by the immunoperoxidase procedure.

The AJ2 antigen was precipitated from cell extracts after labeling with [$^3$H]glucosamine, [$^{35}$S]methionine, or $^{125}$I; all 14 cell lines examined, including melanomas, astrocytomas, carcinomas and leukemias, were positive when tested by one or more labeling method. The dominant component had a MW of 125–140K, depending on the cell line; this was the only component labeled with [$^3$H]-glucosamine. Other subunits were also present, but the number and size varied depending on the cell line. The AJ2 antigen bound to Con A-Sepharose and was eluted with alpha-methyl mannoside. The subunit composition of the AJ2 antigen has been examined most thoroughly in the immunizing cell line, SK-MG-1, using $^{125}$I-labeled cell extracts. Two dimensional electrophoresis showed that the antigen is composed of 4 chains having MW of 170K, 140K, 140K and 28K with isoelectric points at pH 5.2, 5.5, 4.7 and 1.7–6.2, respectively. When unreduced samples were run on SDS-PAGE, the light chain was not seen, suggesting that it is linked to one or more of the heavy chains. The disulfide linkage between the subunits was revealed by performing 2-dimensional electrophoresis with or without reduction before or after isoelectric focusing (the first dimensional separation). The results showed that the light chain is probably attached to only one of the 140K MW subunits, the one with pH 5.5, as indicated by: 1) the slower migration rate of only this subunit in unreduced samples and 2) the shift of most of the light chains to beneath the more basic 140K subunit when the sample is run unreduced in the isoelectric focusing direction and then reduced for the SDS-PAGE separation.

AJ2 immunoprecipitation has been performed with thirteen other cell lines, mostly after labeling with [$^{35}$S]methionine. The 25-28K MW light chain is very faintly observed with this isotope, and would not have been recognized without the use of $^{125}$I-labeled samples. Eleven of these cell lines give results similar to SK-MG-1 except for slight variations in molecular weight of the components. The 170K band was not seen in all experiments, but as this was always a faint band, its absence is probably not significant. With two cell lines, however, considerable variation from the standard pattern was observed. Thus, with AO2, an astrocytoma, an additional band at 105K was seen; with MOLT-4, a T cell leukemia, there were two additional strong bands at 115K and 100K. Other astrocytoma and other lymphomas gave results identical to those with SK-MG-1, so this kind of variation does not appear to be a function of cell type.

AJ2 antigen is a dominant antigen in mice immunized with human cells. All 11 sera tested from mice immunized with various human tumor cells or normal fibroblasts precipitated this antigen as a major component on PAGE from [$^{35}$S]methionine labeled cell extracts. The identification of the component precipitated as the AJ2 antigen was established by sequential precipitation, which was performed with labeled extracts from two different cell lines. Thus pre-clearing with mAb AJ2 removed the 140K band, while pre-clearing with another monoclonal of the same Ig subclass, to an unrelated antigen, had no effect. Using [$^{35}$S]methionine labeled extracts of some cell lines, (for example ovarian carcinoma 2774), the AJ2 band was the strongest band precipitated by all mouse anti-human cell sera. Other observations confirmed the highly antigenic nature of the AJ2 antigen in mice. Thus, after a fusion of mouse spleen cells immunized with a human ovarian carcinoma, 15 supernatants were selected solely on the basis of a strong reaction with the immunizing cell line. Six of these supernatants were found to precipitate the AJ2 antigen, as identified on the basis of the three characteristic $^{125}$I-labeled components.

EXAMPLE 2—MA99

A second monoclonal antibody, MA99, obtained after immunization of mice with an ovarian carcinoma, immunoprecipitated the same antigen complex as AJ2 but showed significant differences in its reactivity with some target cells. MA99 is representative of a class of mAb numbering at least six. Precipitation with mAb AJ2 removed the antigen precipitated by mAb MA99, thus confirming their reactivity with the same antigen. MAb MA99 reacted with all adherent target cells tested, but unlike mAb AJ2, was unreactive or weakly positive with most lymphomas and leukemias. Rosetting titers of mAb MA99 on adherent targets were as strong as titers of mAb AJ2 (generally $10^{-5}-10^{-6}$). In addition, the titers of mAb AJ2 on lymphoma and leukemia cells were as strong as the titers on adherent target cells, suggesting that the lack of reactivity of mAb MA99 with lymphomas and leukemias is not due to lower levels of antigen expression on these cells. In immunoprecipitation, mAb MA99 is much less potent that mAb AJ2, requiring 1.0 microliter rather than 0.1 microliter for optimal precipitation, and precipitating much less antigen. Immunoperoxidase staining of tissue sections with mAb MA99 gave less intense staining that with mAb AJ2, although most tissues were weakly positive, but with some tissues only certain cell types were stained. Most striking was the staining of only glomeruli in the kidney. MAb AJ2, in contrast, stained all cells in kidney sections. The difference between AJ2 and MA99 could be due to a difference in affinity, but more likely is due to varying subunit composition or to varying expression of different regions of the molecule.

EXAMPLE 3—MA103

The antigen detected by mAb MA103, like the AJ2 antigen, was found on all human cell lines (Table 1) and in sections of all human tissues. The titers of this antibody in rosetting assays were in the range of $10^{-5}-10^{-7}$, being particularly high on lymphomas and leukemias. VERO monkey kidney cells were negative. By immunofluorescence, the MA103 antigen was also found on all normal blood leukocytes but was not detected on erythrocytes. The antigen could however be detected on human erythrocytes by quantitative absorption analysis, but at a much lower concentration than on other cell types. It was not detected on erythrocytes from the mouse, rat, rabbit, cat, sheep, horse, chicken, Rhesus monkey, baboon, cynamolgus monkey, or chimpanzee.

mAb MA103 precipitated a broad band of MW 50-55K from SK-RC-4 renal carcinoma cells. This component was detected only after [$^{3}$H]glucosamine labeling, and not after labeling with [$^{35}$S]methaionine, [$^{3}$H]leucine or $^{125}$I, which suggests that is a heavily glycosylated glycoprotein. Unreduced samples migrated slightly faster on acrylamide gels. The isoelectric point of the antigen was at pH 4.2-4.5. The antigen determinant detected by mAb MA103 was stable at 100° for at least 5 minutes, as determined by quantitative absorption, and the solubilized antigen heated similarly could still be immunoprecipitated. These properties suggest that the determinant is a carbohydrate; however, experiments to resolve this point have not been conclusive. An antigen released from [$^{3}$H]glucosamine-labeled cells by trypsinization was precipitatable by mAb MA103; the antigen migrated at the dye front in acrylamide gels, indicating that it was a fragment of the original molecule. This experiment indicates that the molecule is a glycoprotein, since it was reduced in size by trypsin, but it does not prove the carbohydrate nature of the determinant recognized since the peptide portion of the trypsinized fragment could also be involved. Pronase digestion of trypsinized preparations abolished all antigenic activity, even though very high concentrations of the treated sample were tested for their ability to inhibit both immune precipitation and rosetting. Attempts to inhibit mAb MA103 with various sugars and to destroy the MA103 antigen with various glycosidases (neuraminidase, beta-galactosidase, alpha-galactosidase, fucosidase, hexosaminidase, and galactose oxidase), were without effect. These results suggest that the determinant might require both carbohydrate and protein portions of the molecule.

EXAMPLE 4—MH99

Antibodies to the MH99 antigen have been produced from five separate fusions from mice immunized with ovarian or uterine carcinoma. mAb MH99, the prototype antibody of this group of at least five mAbs, did not react with melanomas (16 tested), astrocytomas (18 tested) or normal melanocytes by rosetting assays. It reacted with 8/8 ovarian carcinomas, 1/1 uterine carcinoma 9/16 renal carcinomas, 7/7 colon carcinomas, 8/10 breast carcinomas, 5/10 bladder carcinomas, 17/18 lung carcinomas, 3/3 teratocarcinomas, 1/1 cervical carcinoma, 3/3 pancreatic carcinomas, 1/1 choriocarcinomas, 4/6 neuroblastomas, 3/5 normal fibroblast lines and 2/2 normal kidney epithelial lines. Five of eight T-lymphomas or leukemias and one of three myeloid leukemias were positive, while all B lymphomas, null lymphomas and myelomas tested were negative. The African green monkey kidney cell line VERO was positive, and the hamster ovarian cell line CHO was negative (Table I).

By absorption analysis some melanomas and astrocytomas did express the MH99 antigen, so the negative rosetting assay probably indicates either a low level of antigen or poor exposure of the antigenic determinant recognized. Human erythrocytes were negative by absorption analysis. By immunofluorescence, peripheral blood leukocytes were negative.

Using tissue sections, MH99 was negative on brain, spleen, lymph node, and liver but was positive on the thyroid, testes, lung, pancreas, skin, colon, ovary, uterus and kidney. In some tissues only certain epithelial cells were stained, most prominently in the uterus and the kidney, where only collecting tubules and sital tubules were stained. In sections of ovarian carconomas, tumor cells were darkly stained and stromal cells appeared negative.

Two subunits of MW 29K and 38K were immunoprecipitated by mAb MH99, from cells labeled with [$^{35}$S]methionine, [$^3$H]glucosamine or $^{125}$I. The isoelectric points were at pH 6.2–6.7 and 5.9–6.2, respectively, each subunit comprising a series o two to three discrete spots. Unreduced samples migrated in an unusual manner: a single band corresponding to a molecular weight of about 35K was seen. To analyze this band, 2-D PAGE was performed, in which the first dimension was an SDS-PAGE without reduction, followed by a second dimension electrophoresis with reduction. This experiment revealed that the unreduced component contained both of the subunits, strongly suggesting that the subunits are disulfide linked. The reason for the unusual behavior of this molecule in SDS-PAGE is not clear. The MH99 antigenic determinant was destroyed by heating at 100° C. for 5 minutes, as demonstrated by absorption analysis.

Strongly precipitating mouse monoclonal antibodies to widely distributed human antigens have been described. Each one of the specific mAbs described above is representative of a class of mAb which can be produced by the Kohler-Milstein technique given the starting materials. The same class can be produced with starting materials similar those employed in this invention. The resulting antibodies are useful in removing specific antigens from human cell specimens such as solubilized cell extracts preceding immunization of mice. In this way, antibody responses to less strong or weaker or less abundant antigens is enhanced, as discussed above. The AJ2 antibody has been tested for its ability to remove AJ2 antigen from solubilized cell extracts, and it is very effective. AJ2 antigen is a dominant human antigen in mice and all mice immunized with a variety of human cells are found to produce substantial amounts of antibody to this component.

Another major human antigen in immunized mice is HLA-DR or Ia-like antigen. Immunization with cell lines bearing these antigens induces frequent monoclonal antibodies directed to them. Also, immunization of mice with a solubilized human melanoma antigen preparation containing undetectable amounts of HLA-DR antigen resulted in a strong antibody response to HLA-DR (J. Ng and K.O. Lloyd, unpublished observations). It is therefore important to remove such strongly immunogenic components before subsequent immunizations with inocula containing the less strongly (more weakly) antigenic component.

Other strongly antigenic components are useful in the practice of the present invention. Further examples include the T16, T43, T87 and J143 mAb-Ag systems derived from human bladder immunogen [Yves Fradet, et al. PNAS in press and the subject of a recent patent application Ser. No. 474,229 filed Mar. 11, 1983], the $S_{27}$, $V_1$, and $S_{21}$ mAb-Ag systems derived from renal tissue. [Ueda et al. (1981) Proc. Nat'l Acad. Sci. U.S.A. 78 (5122–5126) and the subject of co-pending applications Ser. No. 297, 814 filed Aug. 31, 1981 and Ser. No. 474,224 filed Mar. 11, 1983] and the F-10 and F-17 mAb-Ag systems derived from human lung and the subject of a co-pending application Ser. No. 474,225 filed Mar. 11, 1983.

The subunit diversity of AJ2 antigen is complex, and more experiments are required to fully explicate the situation. The AJ2 antigen on SK-MG-1 comprises four distinct subunits, two of which have a MW of 140K. The major component of 125–140K, which is glycosylated, is the constant feature in all cell types. The diversity seen between cell lines may be due to: 1) variation in glycosylation, which is a common source of variation between cell types (Morishima, Y., et al. (1982) Immunogenetics 15:529; Ogata, S-I, et al. (1982) Arch. Biochem. Biophysics 217:665; Hoessli, D., et al. (1980) Nature 283:576); 2) difference in subunit composition, with different subunits being attached to one or more constant chains; or 3) varying degrees of degradation of an original molecule to yield different sized fragments. MAb MA99 recognizes the same antigenic complex as mAb AJ2 although there are significant differences between their reactivities with various cells and tissues. This variation could be explained if the two antibodies were directed against different subunits of the complex and these subunits were differently expressed in various cell types. Thus it is useful to have more than one mAb against a strong antigenic site, in order to completely react with the site, insuring deactivation of the site.

The MA103 antigen is unusual in that it is a glycoprotein antigen in which the determinant is not denatured by treatment at 100° C. for 5 minutes. Heat stability indicates that the determinant is the carbohydrate moiety of the glycoprotein since heat stable antigens are commonly glycolipids (Pukel, C. S. et al. (1982) J. Exp. Med. 155:1133; Stern, P. L., et al. (1978) Cell 14:775). Antibodies to carbohydrate portions of vertebrate glycoproteins are rare, but have been described (Momoi, M., et al. (1980) J. Biol. Chem. 225: 11914; Clement, L. T., et al. (1981) J. Immunol. 127:1220; Merler, E., et al. (1974) Nature 251:652; Mattes, M. J., et al. (1981) Nature 273: 761). However, glycopeptides generated by pronase digestion could not be shown to react with MA103. The reason for this is not fully understood. However, it is believed one explanation is if the antigen contains multiple similar carbohydrate structures and if divalent attachment of the antibody is required to allow immunoprecipitation. Another explanation is that the MA103 determinant is composed of both carbohydrate and protein portions which interact in a heat stable manner. This antigen resembles the hexose transporter protein (Gorga, F. R., et al. (1979) Biochem. Biophys. Res. Common. 91:955) in its molecular weight, in the broad band seen in SDS-PAGE, in being heavily glycosylated and in its widespread distribution. Also, like the hexose transporter, the MA103 antigen was degraded by the endo-beta-galactosidase from *Escherichia freundii* (Miles Laboratories, Elkhart, In.), yielding a product of MW 35-40K. The nucleoside transporter is similar in some respects (Young, J. D., et al. (1982) J. Biol. Chem. 258:2202) and is another potential identity for MA103.

MH99 antigen is found on many but not all cell types, and its distribution is related to histologic type. The subunit structure is similar to that of human HLA-DR antigens (Lloyd, K. O., et al. (1981) Supra) except that the chains are disulfide bonded. The fact that it is present on some T lymphomas and myeloid leukemias, but not B lymphomas, is of interest, since HLA-DR antigens, in general, have the inverse distribution. An unusual characteristic of the MH99 antigen is its migration in unreduced SDS-PAGE, in that it migrates approximately twice as fast as expected from its molecular weight. Since expression of MH99 subdivides most types of carcinomas, MH99 can be useful in tumor subclassification which is valuable in prognosis and in selecting therapy options.

Although the antigens with which they react are present on a majority of human cell specimens, the mAbs MH99, MA103, MA99 do not react with blood group antigens such as A, B, H, Le$^a$, Le$^b$, X, y or I.

Monoclonal antibodies MA 103, MH 99, MA 99, AJ2, J143, T16, T43, T87, HLA-DR, S$_{27}$, S$_{21}$ and B$_1$ are on deposit and available at Sloan-Kettering Institute, 1275 York Avenue, New York, N.Y. 10021.

Monoclonal antibodies MA 99, MH 99 and MA 103 have been deposited with the Americana Type Culture Collection (ATCC) (Registered Trademark)], 12301 Parklawn Drive, Rockville, Md. 20852 on Oct. 28, 1983, a recognized depository, and have been given ATCC Accession numbers of HB 8407 for mAb 99, HB 8406 for mAb MH 99 and HB 8408 for mAb MA 103.

Monoclonal antibodies S$_{27}$, S$_{21}$ and V$_1$ have been deposited with the ATCC on Nov. 15, 1983 and have been given ATCC accession numbers of HB 8428 for mAb S$_{27}$, HB 8247 for mAb S$_{21}$ and HB 8429 for mWAb V$_1$.

Monoclonal antibody J143, T16, T43 and T87 were deposited with the ATCC on Mar. 11, 1983 and were given ATCC accession numbers of HB8276 for J143, HB8279 for T16, HB8275 for T43 and HB8274 for T87.

Monoclonal antibodies AJ2 was deposited with the ATCC on Aug. 16, 1983 and has an ATCC accession number HB 8338.

Monoclonal antibodies F-10 and F-17 were deposited with the ATCC on Mar. 11, 1983 and were given ATCC accession numbers of HB 8261 for F-10 and HB8267 for F-17.

What is claimed is:

1. The hybridoma cell line designated MA 103 having A.T.C.C. Accessories No. HB 8408.
2. The hybridoma cell line designated MH 99 having A.T.C.C. Accession No. HB 8406.
3. The hybridoma cell line designated MA 99 having A.T.C.C. Accession No. HB 8407.
4. The monoclonal antibody produced by the hybridoma cell line of claim 1.
5. The monoclonal antibody produced by the hybridoma cell line of claim 2.
6. The monoclonal antibody produced by the hybridoma cell line of claim 3.

* * * * *